United States Patent
Tohmeh et al.

(10) Patent No.: US 8,936,626 B1
(45) Date of Patent: Jan. 20, 2015

(54) BI-CORTICAL SCREW FIXATION

(71) Applicant: NuVasive, Inc., San Diego, CA (US)

(72) Inventors: Antoine G. Tohmeh, Spokane, WA (US); Fernando Olea, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/771,076

(22) Filed: Feb. 19, 2013

Related U.S. Application Data

(60) Provisional application No. 61/600,576, filed on Feb. 17, 2012.

(51) Int. Cl.
*A61B 17/70* (2006.01)
*A61B 17/88* (2006.01)

(52) U.S. Cl.
CPC .................................. *A16B 17/7076* (2013.01)
USPC ......................................... 606/279; 606/86 A

(58) Field of Classification Search
CPC ........... A61B 17/7032; A61B 17/1671; A61B 17/7037; A61B 17/7082; A61B 17/7011; A61B 17/8811; A61B 17/863; A61B 17/864; A61B 17/8891; A61B 17/3417; A61B 17/3421; A61B 17/1757; A61B 2017/0256; A61B 17/7076
USPC ....... 606/279, 304, 305, 86 A, 104, 251, 301, 606/246
See application file for complete search history.

(56) References Cited

U.S. PATENT DOCUMENTS

| | | |
|---|---|---|
| 4,655,216 A | 4/1987 | Tischer |
| 5,720,751 A | 2/1998 | Jackson |
| 6,139,549 A | 10/2000 | Keller |
| 6,183,472 B1 | 2/2001 | Lutz |
| 6,235,028 B1 | 5/2001 | Brumfield et al. |
| 6,299,616 B1 | 10/2001 | Beger |
| 6,379,364 B1 | 4/2002 | Brace et al. |
| 6,440,133 B1 | 8/2002 | Beale et al. |
| 6,511,484 B2 | 1/2003 | Torode et al. |
| 6,530,929 B1 | 3/2003 | Justis et al. |
| 6,547,795 B2 | 4/2003 | Schneiderman |
| 6,648,888 B1 | 11/2003 | Shluzas |
| 6,929,606 B2 | 8/2005 | Ritland |
| 6,951,538 B2 | 10/2005 | Ritland |
| 7,008,422 B2 | 3/2006 | Foley et al. |
| 7,011,660 B2 | 3/2006 | Sherman |
| 7,179,261 B2 | 2/2007 | Sicvol et al. |
| 7,188,626 B2 | 3/2007 | Foley et al. |
| 7,481,813 B1 | 1/2009 | Purcell |
| 7,657,308 B2 | 2/2010 | Miles et al. |
| 7,664,544 B2 | 2/2010 | Miles et al. |
| 7,942,826 B1 | 5/2011 | Scholl et al. |
| 2001/0021853 A1 | 9/2001 | Heckele et al. |
| 2002/0026195 A1 | 2/2002 | Layne et al. |
| 2003/0199872 A1 | 10/2003 | Markworth et al. |
| 2003/0208203 A1 | 11/2003 | Lim et al. |
| 2003/0229354 A1 | 12/2003 | Schmieding et al. |
| 2004/0138662 A1 | 7/2004 | Landry et al. |
| 2004/0143265 A1 | 7/2004 | Landry et al. |

(Continued)

*Primary Examiner* — Pedro Philogene
(74) *Attorney, Agent, or Firm* — Jonathan Spangler; Rory Schermerhorn

(57) ABSTRACT

Surgical systems and methods are disclosed for safe bi-cortical bone screw placement within a bone segment. Included is a method of measurement to control advancement of instruments and implants to repeatedly obtain bi-cortical screw fixation while minimizing protrusion of the lead end of the screw beyond the distal cortical wall therein reducing incidence of injury to adjacent soft tissues.

10 Claims, 14 Drawing Sheets

(56) References Cited

U.S. PATENT DOCUMENTS

| | | |
|---|---|---|
| 2004/0147937 A1 | 7/2004 | Dunbar, Jr. et al. |
| 2004/0172022 A1 | 9/2004 | Landry et al. |
| 2005/0021031 A1 | 1/2005 | Foley et al. |
| 2005/0065517 A1 | 3/2005 | Chin |
| 2005/0085813 A1 | 4/2005 | Spitler et al. |
| 2005/0131408 A1 | 6/2005 | Sicvol et al. |
| 2005/0131419 A1 | 6/2005 | McCord et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0154389 A1 | 7/2005 | Selover et al. |
| 2005/0192570 A1 | 9/2005 | Jackson et al. |
| 2005/0192579 A1 | 9/2005 | Jackson |
| 2005/0192589 A1 | 9/2005 | Raymond et al. |
| 2005/0215999 A1 | 9/2005 | Birkmeyer et al. |
| 2005/0228380 A1 | 10/2005 | Moore et al. |
| 2005/0228400 A1 | 10/2005 | Chao et al. |
| 2005/0245928 A1 | 11/2005 | Colleran et al. |
| 2005/0251139 A1 | 11/2005 | Roh |
| 2006/0003624 A1 | 1/2006 | Dow et al. |
| 2006/0036244 A1 | 2/2006 | Spitler et al. |
| 2006/0036255 A1 | 2/2006 | Pond, Jr. et al. |
| 2006/0069391 A1 | 3/2006 | Jackson |
| 2006/0074418 A1 | 4/2006 | Jackson |
| 2006/0079894 A1 | 4/2006 | Colleran et al. |
| 2006/0079909 A1 | 4/2006 | Runco |
| 2006/0084993 A1 | 4/2006 | Landry et al. |
| 2006/0089651 A1 | 4/2006 | Trudeau et al. |
| 2006/0095035 A1 | 5/2006 | Jones et al. |
| 2006/0106380 A1 | 5/2006 | Colleran et al. |
| 2006/0106394 A1 | 5/2006 | Colleran et al. |
| 2006/0111712 A1 | 5/2006 | Jackson |
| 2006/0111715 A1 | 5/2006 | Jackson |
| 2006/0122597 A1 | 6/2006 | Jones et al. |
| 2006/0142761 A1 | 6/2006 | Landry et al. |
| 2006/0200132 A1 | 9/2006 | Chao et al. |
| 2006/0247658 A1 | 11/2006 | Pond, Jr. et al. |
| 2006/0264934 A1 | 11/2006 | Fallin |
| 2006/0281838 A1 | 12/2006 | Steinhausler et al. |
| 2006/0293693 A1 | 12/2006 | Farr et al. |
| 2007/0049931 A1 | 3/2007 | Justis et al. |
| 2007/0167949 A1 | 7/2007 | Altarac et al. |
| 2007/0167954 A1 | 7/2007 | Sicvol et al. |
| 2007/0233155 A1 | 10/2007 | Lovell |
| 2008/0005787 A1 | 1/2008 | Aldred |
| 2008/0024937 A1 | 1/2008 | Gill et al. |
| 2008/0051787 A1 | 2/2008 | Remington et al. |
| 2008/0073323 A1 | 3/2008 | Full et al. |
| 2008/0077135 A1 | 3/2008 | Stad et al. |
| 2008/0077138 A1 | 3/2008 | Cohen et al. |
| 2008/0091213 A1 | 4/2008 | Jackson |
| 2008/0132904 A1 | 6/2008 | Suher et al. |
| 2008/0140132 A1 | 6/2008 | Perez-Cruet |
| 2008/0172062 A1 | 7/2008 | Donahue et al. |
| 2008/0275456 A1 | 11/2008 | Vonwiller et al. |
| 2008/0288005 A1 | 11/2008 | Jackson |
| 2008/0312703 A1 | 12/2008 | Hestad et al. |
| 2008/0319477 A1 | 12/2008 | Justis et al. |
| 2009/0171391 A1 | 1/2009 | Hutton et al. |
| 2009/0048601 A1 | 2/2009 | Forton et al. |
| 2009/0082666 A1 | 3/2009 | Geist et al. |
| 2009/0099572 A1 | 4/2009 | Geist et al. |
| 2009/0131755 A1 | 5/2009 | White et al. |
| 2009/0143828 A1 | 6/2009 | Stad et al. |
| 2009/0216234 A1 | 8/2009 | Farr et al. |
| 2009/0254131 A1* | 10/2009 | Roh ............................ 606/86 A |
| 2010/0004696 A1 | 1/2010 | Jackson |
| 2010/0036495 A1 | 2/2010 | Daum et al. |
| 2010/0331883 A1 | 12/2010 | Schmitz et al. |
| 2011/0230965 A1 | 9/2011 | Schell et al. |
| 2012/0022597 A1* | 1/2012 | Gephart et al. ............... 606/279 |
| 2012/0265250 A1 | 10/2012 | Ali |
| 2013/0072986 A1* | 3/2013 | Robinson ..................... 606/279 |

* cited by examiner

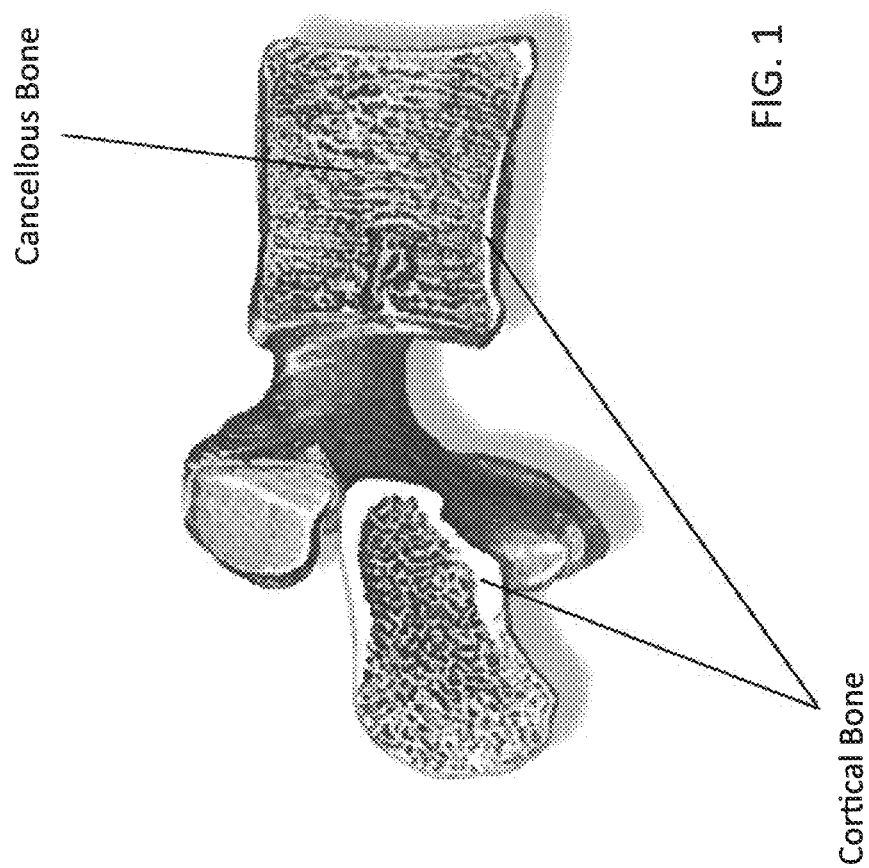

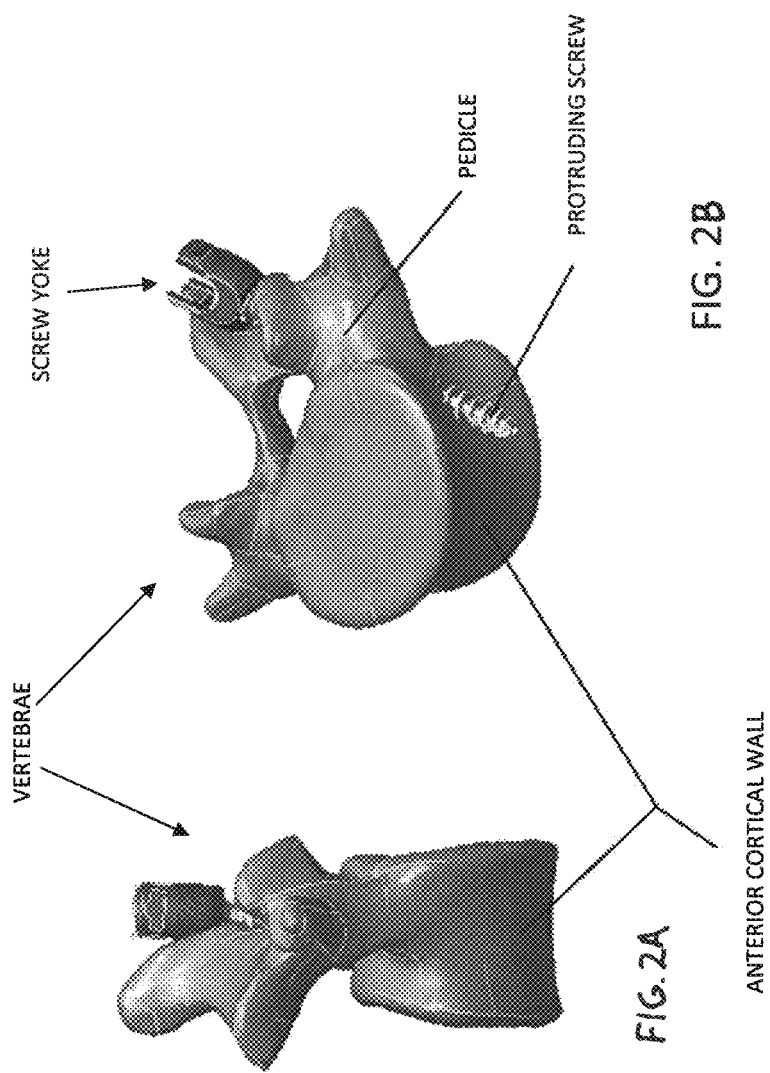

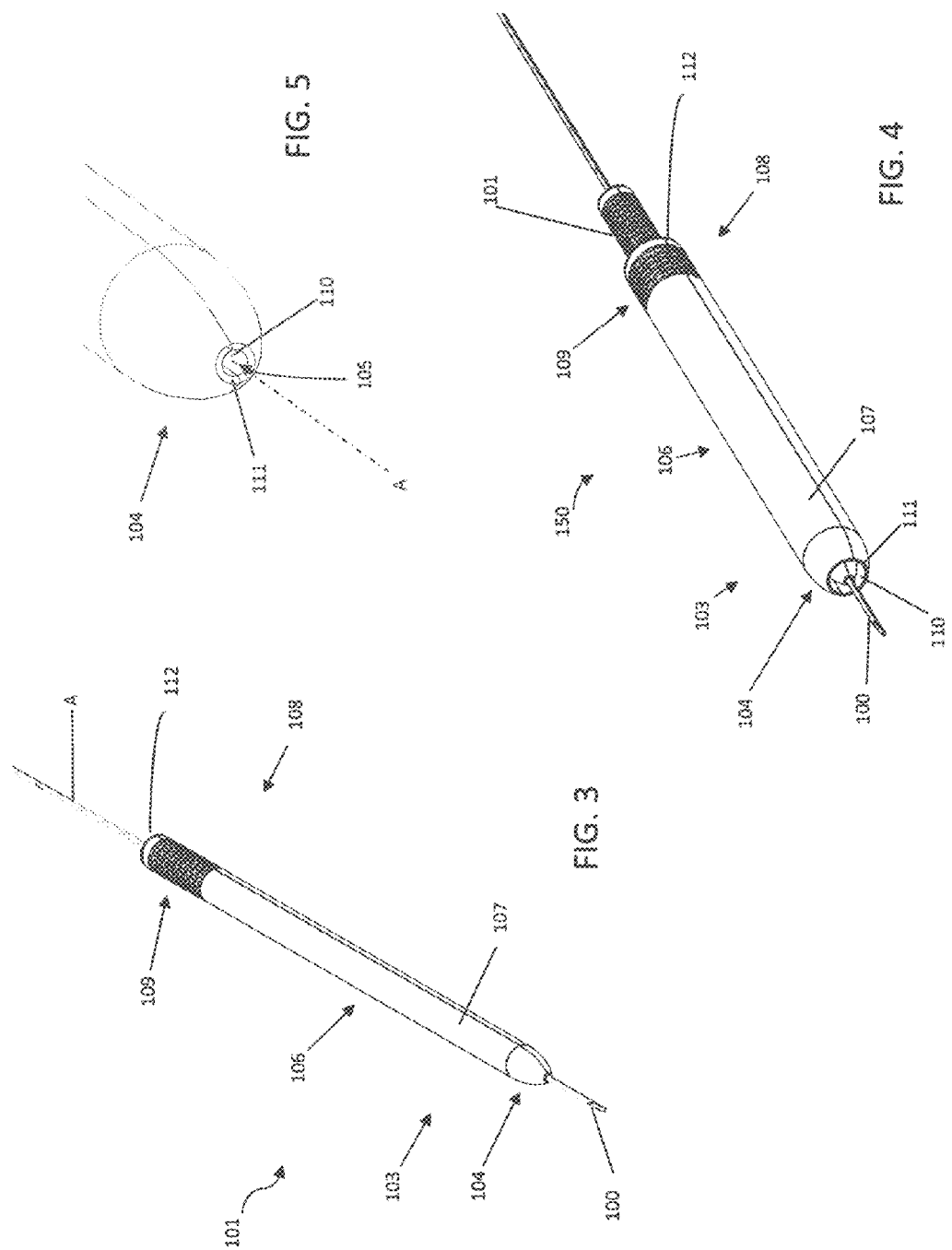

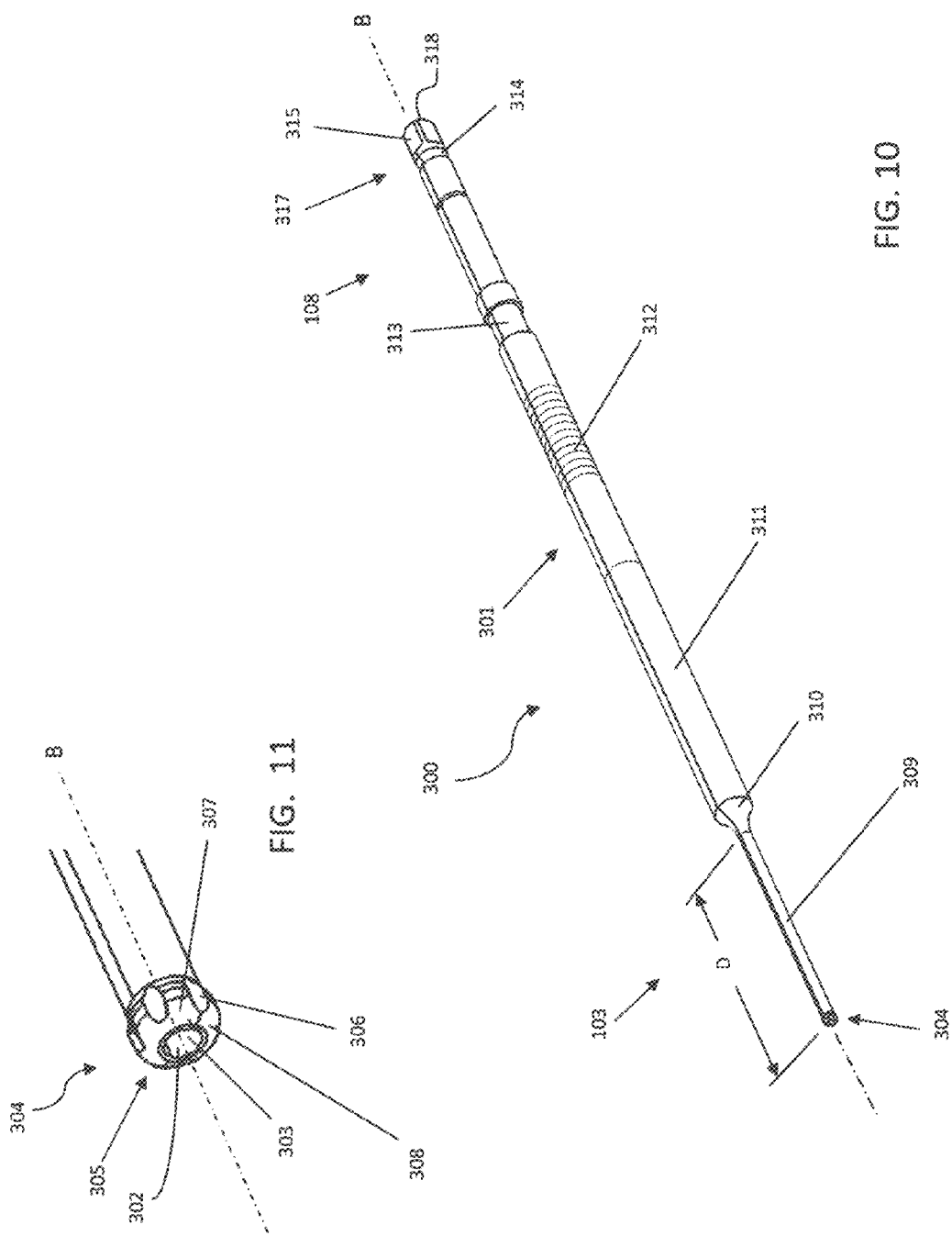

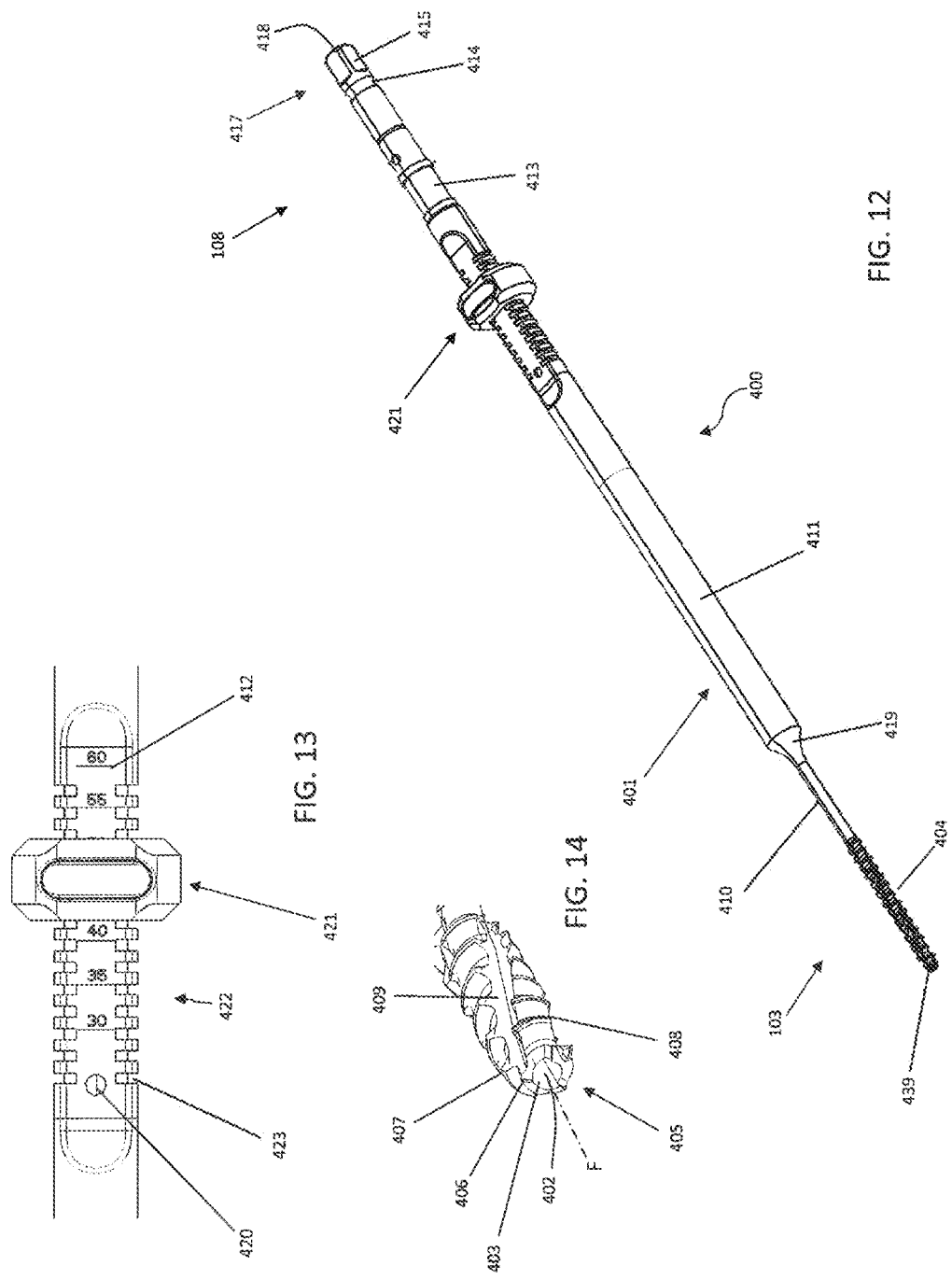

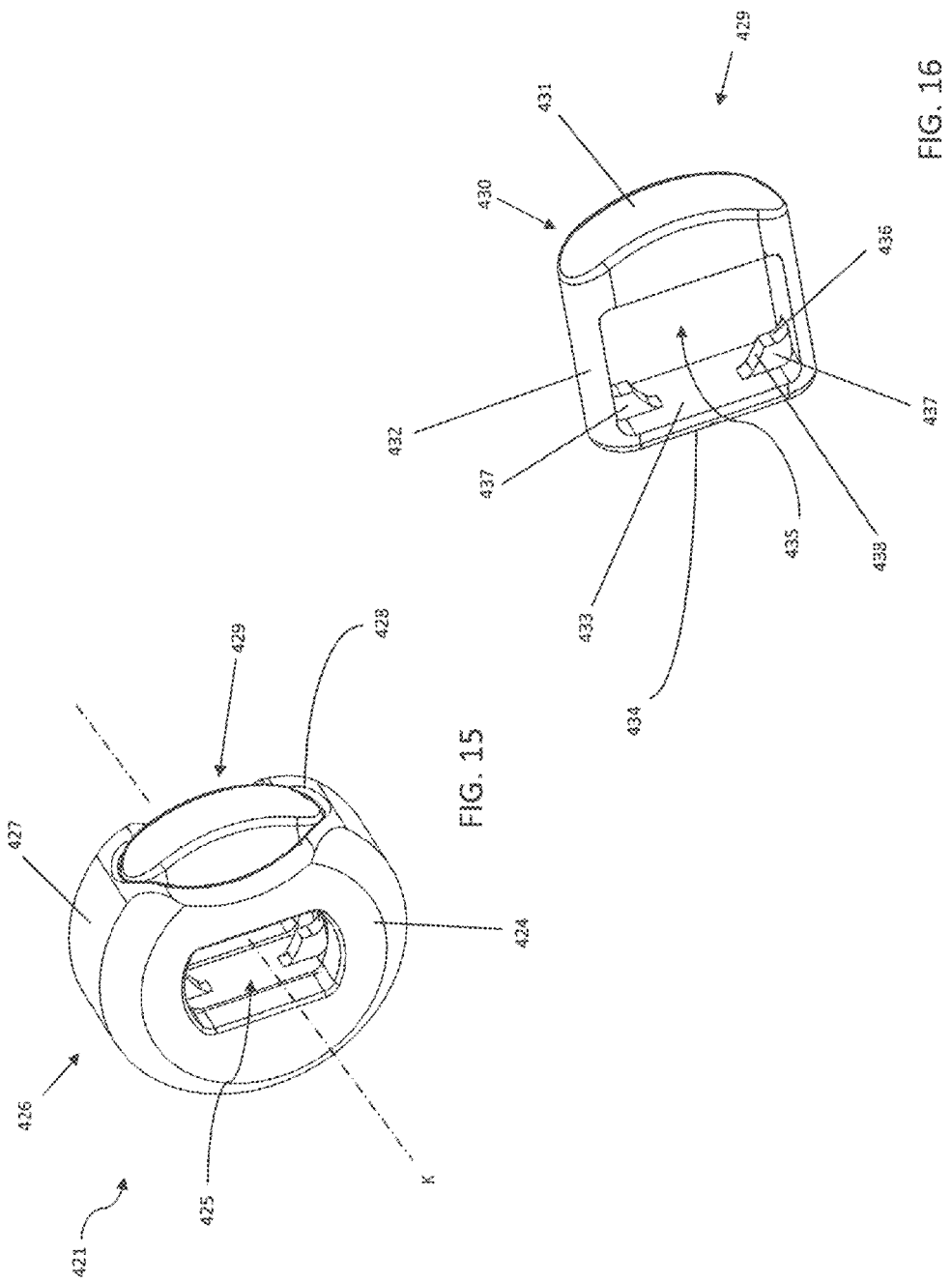

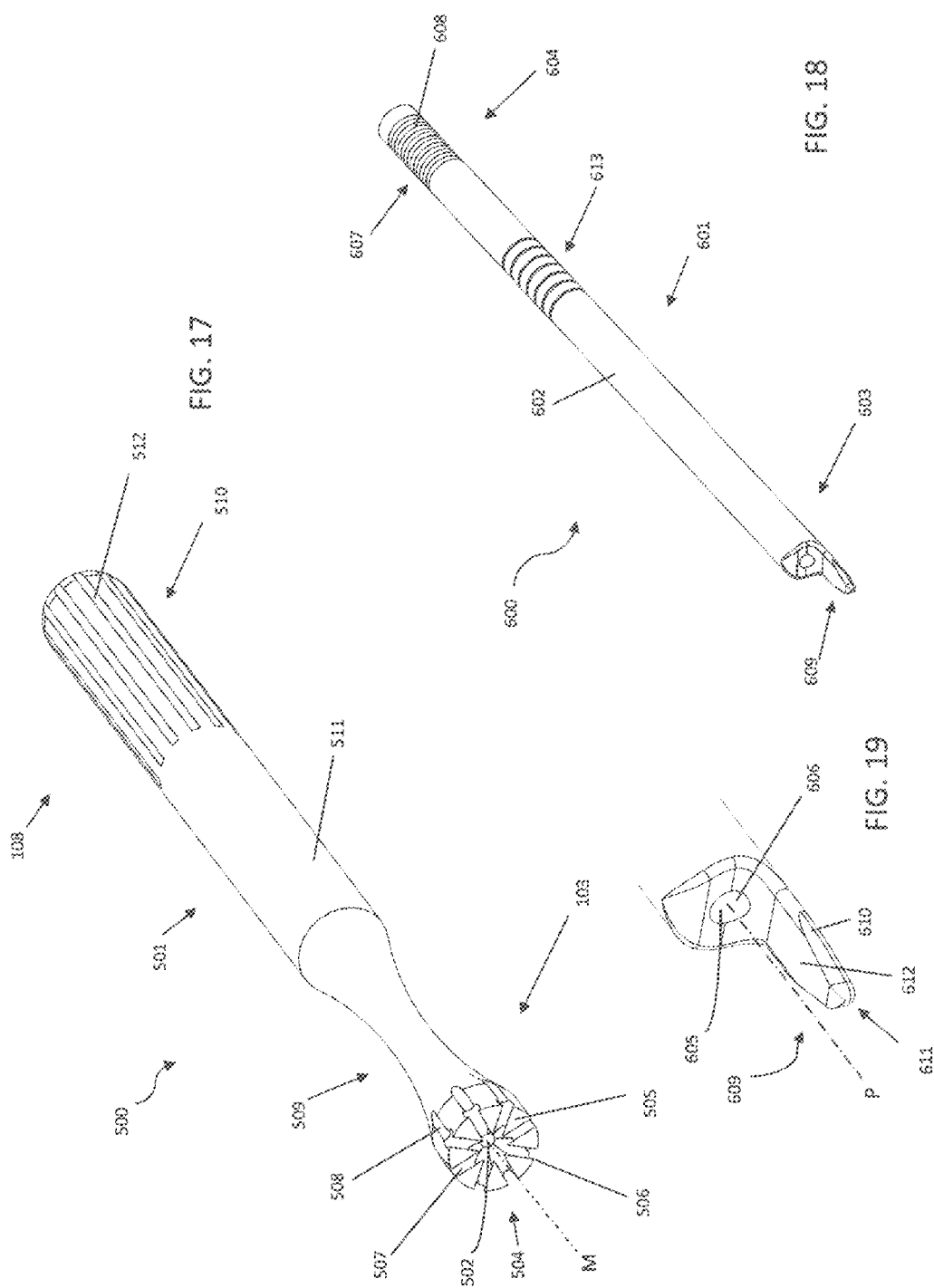

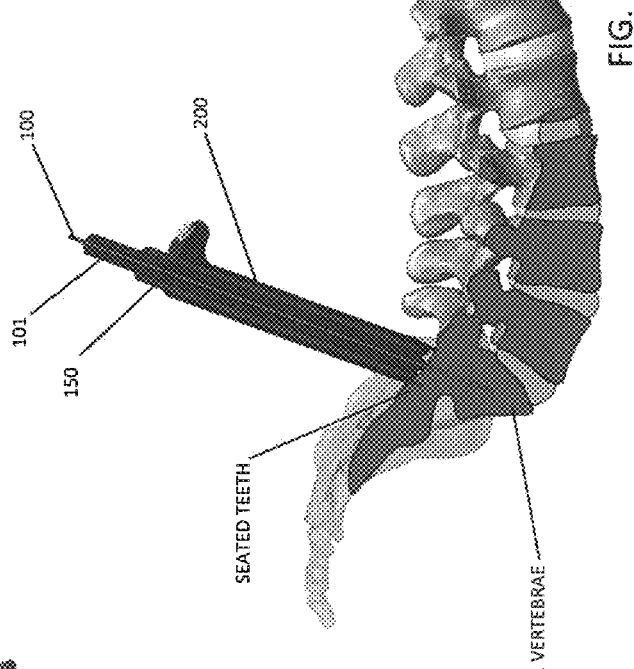
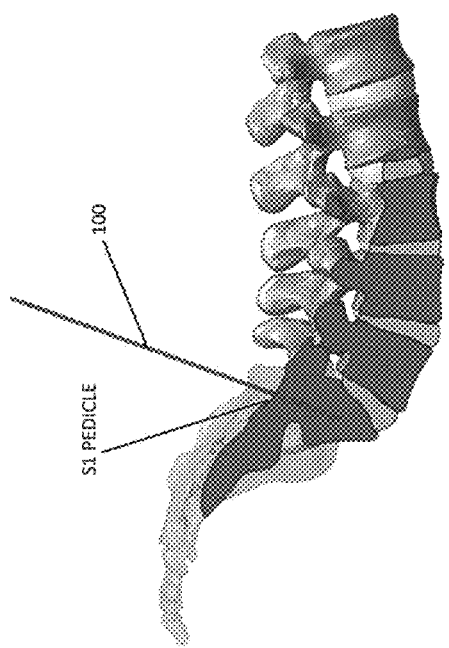

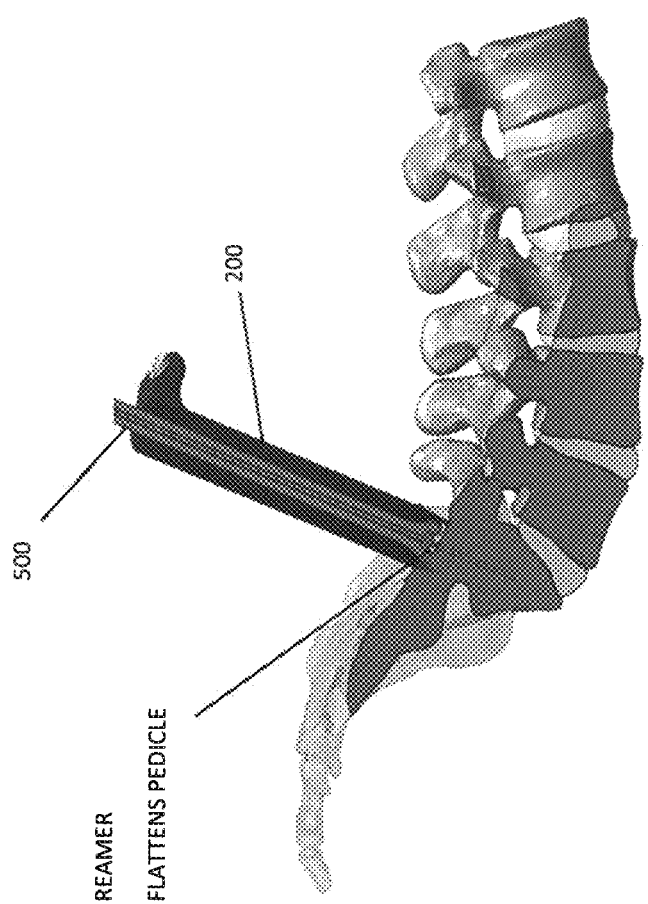

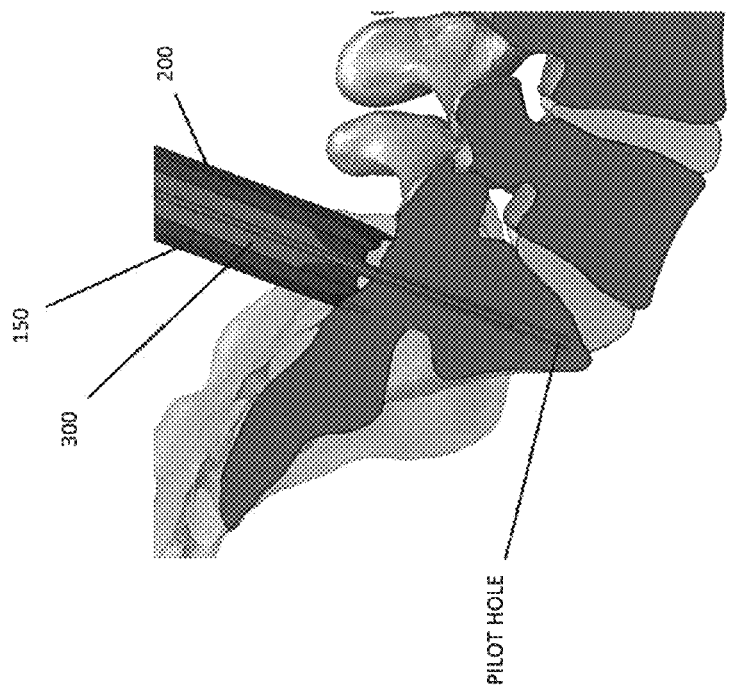
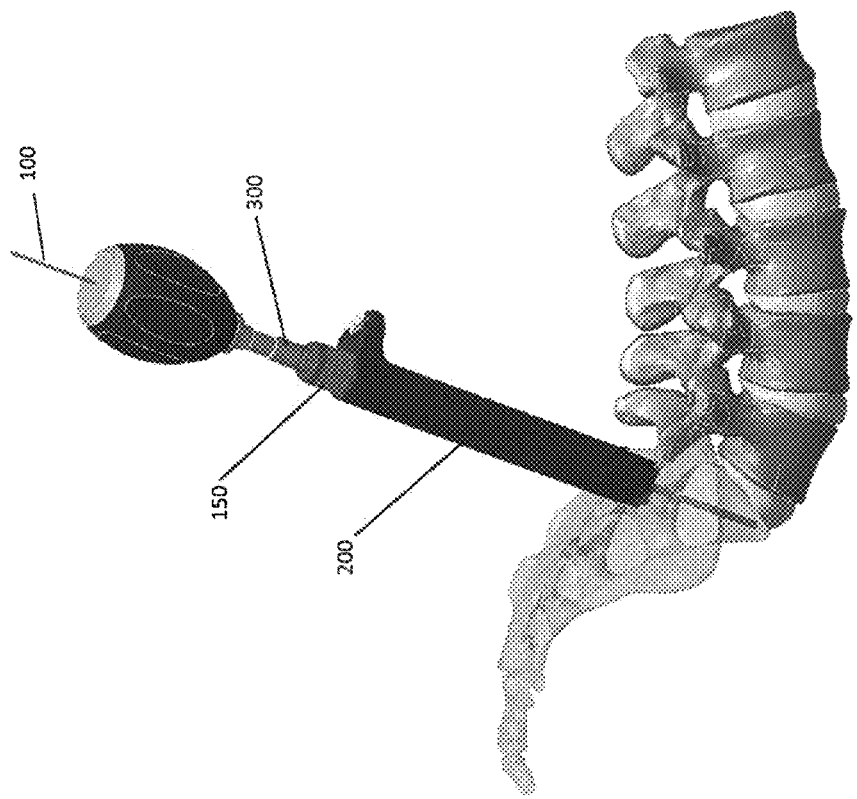

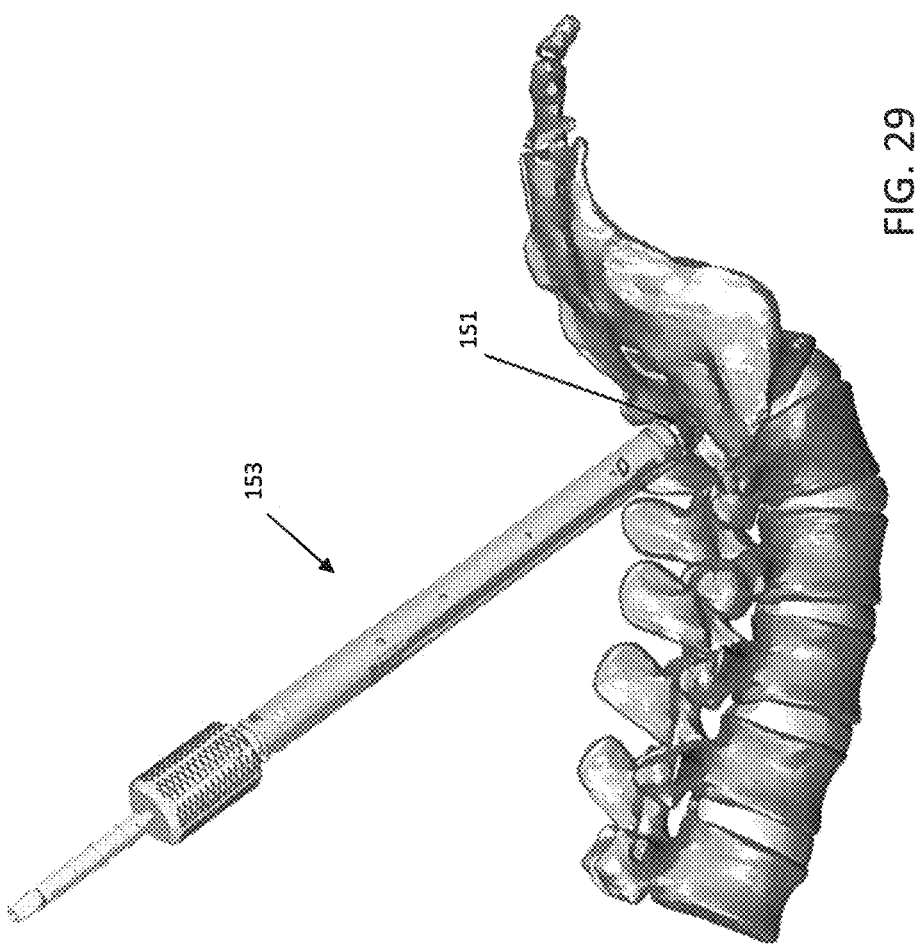

BI-CORTICAL SCREW FIXATION

CROSS REFERENCES TO RELATED APPLICATIONS

The present application is a utility patent application that claims priority to U.S. Provisional Application Ser. No. 61/600,576, filed on Feb. 17, 2012, the entire contents of which are hereby expressly incorporated by reference into this disclosure as if set forth fully herein.

FIELD

This application describes surgical instruments and methods for performing bi-cortical pedicle fixation.

BACKGROUND

Bones consist of cancellous bone covered by a thin layer of cortical bone as illustrated in FIG. 1. Cancellous bone is a sponge-like bone structure which is less dense, softer, and weaker when compared to cortical bone. Bone screws are utilized in surgery typically to stabilize and fix bone segments or to use as an anchor site within the bone. Most commonly, the screws are advanced through the outer cortical wall and anchored into the cancellous bone within. However, bi-cortical fixation can be used to achieve greater purchase, as the screw is fixed within the stronger cortical bone at two separate points, the proximal and distal ends of the screw. Doing so increases the screw's pull out strength, which may be desirable at higher load levels, such as in the lower lumbar and sacrum of the spine.

Safely achieving bi-cortical screw purchase is often difficult however. In the human vertebrae for example, the goal of bi-cortical pedicle screw fixation is to reach and thread the lead end of the screw into the anterior cortical wall. If the tip of the screw or associated instrumentation is advanced too far beyond the anterior cortical wall, the vital tissues that reside adjacent the anterior wall of the vertebrae, the great vessels for example, may be put at risk. Even with utilization of intraoperative fluoroscopy, safely gauging a screw's position can be difficult. As illustrated in FIG. 2, the curvature of the anterior cortical wall of the vertebral body may cause difficulty correctly determining the position of a screw from a lateral view, such that in the lateral fluoroscope image the distal end of the screw may appear to be contained within the vertebra since the final depth of the distal end may be less than the vertebral depth at the anterior most portion (FIG. 2A). However, the actual screw position, FIG. 2B, is such that the distal end of the screw protrudes beyond the anterior cortical wall but at a position where the depth of the wall is less than the greatest depth near the center.

Current methods of bi-cortical screw fixation rely heavily on surgeon feel when forming and/or tapping the pilot hole through the vertebral body and/or during screw insertion. Thus, a need exists for instruments and methods to facilitate bi-cortical implantation of bone anchors.

SUMMARY

In preferred embodiments, the method of bi-cortical screw fixation utilizes a system of instruments with implants to achieve safe and repeatable bi-cortical fixation of screws. The method may be used for bi-cortical fixation in most bone segments and is well suited for use when securing pedicle screws in a vertebral body. In a preferred embodiment, a method is described for use in the sacrum.

The method begins by placement of a K-wire through the posterior cortical wall of a vertebral pedicle, via a Jamsheedi needle. One or more dilators are then inserted over the K-wire to dilate the tissues adjacent the K-wire. In this preferred example, the dilators include a first, second, and third dilator of increasingly larger diameter. The dilators are advanced until their lead end contacts the bone surface of the pedicle.

Optionally, a contour probe with reference scale may be advanced through the outer (e.g. third) dilator (after removal of the first and second dilators) to the pedicle. This instrument will assist the surgeon in measuring the magnitude of surface irregularity at the pedicle. The surgeon can then determine if there is a need for use of a bone reamer to create a flat pedicle surface and to gauge the depth of reaming desired. If needed, a cannulated bone reamer is guided down the K-wire and rotated sufficiently against the bone to the predetermined depth therein creating a uniform bone surface at the pedicle site. The resulting flat pedicle surface situated perpendicular to the guide wire serves as a level seat for the distal end of the second dilator, increasing the accuracy (if necessary) with which an exposed proximal end of the dilator can be used as reliable reference point to measure the depth of the vertebra later in the technique. Upon removal of the reamer, bone shavings may be removed by suction or other instruments. The second dilator is reinserted into the third dilator and advanced until seated against the bone or newly created uniform bone surface.

A cannulated blunt-tip probe is advanced over the guide wire and down the second dilator into the cortical wall pilot hole created by the Jamsheedi needle. As the name implies, the probe includes a blunted tip suitable to burrow through the cancellous bone within the vertebral body, extending the pilot hole and establishing a desired trajectory through the vertebra. While the blunt-tip probe effectively traverses through the softer cancellous bone, the probe is ineffective at puncturing the denser cortical bone. Thus, when the probe tip arrives at the anterior cortical wall, the probe experiences a hard stop and further advancement of the probe is inhibited. With the blunt-tip probe traversing the depth of the pedicle, reference markers near the proximal end of the probe are consulted (relative to the end of the dilator) to determine the depth to the anterior cortical wall, which can be later used to determine the desired tap depth and screw length.

With the blunt-tip probe defining the pilot hole trajectory, the third dilator is preferably fixed in position in alignment with the pilot hole trajectory. Fixing of the dilator may be achieved by attachment of a fixing arm to a fixator portion on the third dilator. The fixing arm may take several forms such as an A-arm attached to the operating table or other fixed device. Fixedly aligning the dilator with the pilot hole trajectory advantageously allows the K-wire to be removed during the subsequent tapping and screw insertion steps.

With the K-wire and blunt-tip probe removed, a tap is advanced through the second dilator which ensures alignment with the previously prepared pilot hole (by virtue of being constrained within the third dilator, which has a fixed trajectory; the second dilator is also fixed). Armed with the previously determined depth measurement, the desired tap depth to penetrate and tap the cortical wall without extending too far beyond the cortical wall can be determined, allowing for controlled piercing of the cortical wall. An adjustable safety stop on the tap is used to control the depth to which the tap can be received through the second dilator and thus also, the depth the tap can advance through the vertebra. Though these steps have been described with reference to a tap, in instances where self-tapping screws are used, the tap may be replaced with an awl including the same depth controlling features as the described tap.

The desired size pedicle screw may be chosen based on the determined depth of the vertebra. The pedicle screw is attached to the screw inserter then advanced down the third dilator (the second dilator having been removed) and under rotation advanced through the bone until reaching the desired bi-cortical position. The screw inserter may also include reference markings and/or adjustable depth stop as still an additional feature for controlling screw depth.

Reference markings on the instruments may be in a variety of forms, including numbers reflective of relative distances or depths, hash marks, grooves, ridges, color codes, or other visual or tactile indicator capable of providing measurement or sizing feedback to the user. The reference markings may represent a specified depth, or direct the user to a particular screw size or instrument choice.

BRIEF DESCRIPTION OF THE DRAWINGS

FIG. 1 is a cross-sectional view along a median sagittal plane of a human vertebra.

FIG. 2A is a lateral view representative of a false negative indication of cortical wall breach that is possible on a lateral fluoroscopic image.

FIG. 2B is a perspective view of the vertebra and screw of FIG. 2A, illustrating the actual position of the pedicle screw extending beyond anterior cortical wall.

FIG. 3 is a front perspective view of an example embodiment of a first dilator with a K-wire.

FIG. 4 is a front perspective view of an example embodiment of a second dilator concentrically positioned over the first dilator and K-wire of FIG. 3.

FIG. 5 is a front perspective view of the nose of the first dilator of FIG. 3.

FIG. 10 is a front perspective view of an example embodiment of a blunt-tip probe.

FIG. 11 is a front perspective close up view of the blunt tip of the probe illustrated in FIG. 10.

FIG. 12 is a front perspective view of an example embodiment of a bone tap with safety stop.

FIG. 13 is a close up view of a distal portion of the tap of FIG. 12 with the safety stop mechanism.

FIG. 14 is a front perspective close up view of the tap tip of FIG. 12.

FIG. 15 is a front perspective view of an example embodiment of a tap's safety stop assembly.

FIG. 16 is a front perspective view of a release used within a safety stop.

FIG. 17 is a front perspective view of an example embodiment of a bone reamer.

FIG. 18 is a front perspective view of an example embodiment of a pedicle contour probe.

FIG. 19 is a front perspective close up view of the tip of the probe in FIG. 18.

FIG. 22 is a cross-sectional sagittal plane view through the pedicles of the lumbar spine illustrating proper placement of a guidewire, according to one example method for achieving bi-cortical screw fixation using the instruments of FIGS. 3-21.

FIG. 23 is a cross-sectional sagittal plane view through the pedicles of the lumbar spine illustrating placement of an first dilator, a second dilator, and a third dilator against the bone segment, according to the example method.

FIG. 24 is a cross-sectional sagittal plane view through the pedicles illustrating insertion of the reamer, according to the example method referenced in FIG. 23.

FIG. 25 is a lateral view of a blunt tip probe creating a pilot hole in the vertebrae, according to the example method referenced in FIG. 23.

FIG. 26 is a cross-sectional sagittal plane view through the pedicles of FIG. 25 illustrating the blunt tip probe creating a pilot hole in the vertebrae.

FIG. 29 is a lateral view of the spine illustrating a pedicle screw with attached insertion instruments advanced into the pedicle, according to the example method referenced in FIG. 23.

DETAILED DESCRIPTION

Figure 9:
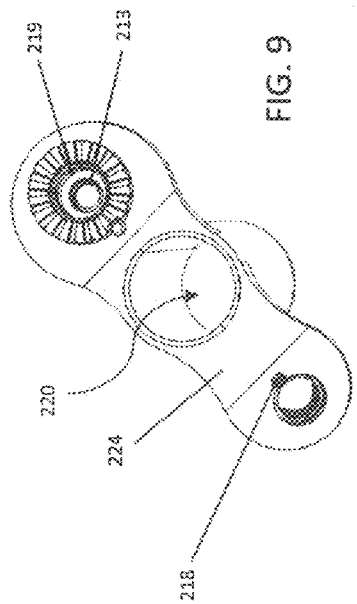
FIG. 9 is a top perspective view of the third dilator of FIG. 6.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system and method for performing bi-cortical pedicle fixation disclosed herein boasts a variety of inventive features and components that warrant patent protection, both individually and in combination.

The present application describes a instruments and methods for performing bi-cortical pedicle fixation. Several instruments are utilized in the method disclosed herein for bi-cortical screw fixation. FIGS. 3-21 illustrate various example embodiments of instruments used during the later described method. FIG. 3 illustrates a first dilator advanced to the target pedicle (e.g. the S1 pedicle) over a K-wire (the K-wire having been positioned in the pedicle using a jamsheedi needle, not shown). After placement of the K-wire 100 (or similar guide wire) at the predetermined position in the bone, a plurality of dilators are used to dilate the tissues surrounding the K-wire to provide access to the pedicle. The K-wire defines an elongated axis 'A' that serves as a surgical guide path through the body to the entry point on the pedicle.

The dilator having the smallest outer diameter is the first dilator 101 comprising an elongated tube body 106 of sufficient length to extend from the surface of the bone to a distance above the skin. An outer surface 107 of dilator 101 resides on the exterior of the dilator body 106. This surface 107, preferably smooth, slides along the soft tissues of the body while radially stretching them to provide passage of the first dilator 101 down to the bone segment.

At the distal or lead end 103 portion of the first dilator 101 is the nose 104 portion. The nose 104 is preferred to be of a rounded cone or bullet shape. As the first dilator 101 is advanced, the surface of the leading smaller diameter portion of the nose 104 begins to gradually dilate the surrounding tissues to the full diameter of the nose 104.

Central to the nose is an aperture 105 that extends the length of the first dilator 101 and defines an inner elongated wall 110 of the dilator 101 as illustrated in FIG. 5. The aperture 105 is of a diameter slightly larger than the K-wire 100 such that the first dilator 101 can freely slide down the wire 100 without permitting ingress of tissue between the dilator and K-wire. The aperture 105 diameter may increase in diameter as it moves along the body 106 towards the proximal end 108 portion to prevent binding between the K-wire and the inner walls 110 of the aperture 105. At the distal end of the nose 104, is distal stop surface 111 that abuts against the bone when fully advanced down surgical path A.

A grip portion 109 may be included on or inscribed into surface 107 at the proximal end 108 of elongated body 106. The grip portion 109 may take a variety of forms to improve the surgeon's grasp on the dilator 101 as the dilator is directed toward the bone segment. In the example embodiment shown, the grip 109 is in the form of a knurled surface but alternatively may be in the form of a polymer sleeve pulled over a recessed area of the elongated body 106. At the proximal end is proximal stop surface 112.

FIG. 4 illustrates a second dilator 150 of the plurality of dilators, an intermediate dilator placed concentrically over the first dilator 101 and K-wire/guidewire 100. The second dilator 150 in this preferred embodiment is a replica of the first dilator 101 but varies dimensionally in diameter and length. For example, the inner elongated wall 110 of the second dilator 150 is sized slightly larger in diameter than outer diameter of body 106 of the first dilator 101 wherein the second dilator 150 will glide over the first dilator 101. Similarly, the body 106 of second dilator 150 comprises an outer diameter slightly smaller than the inner wall 110 of the third dilator 200 illustrated in FIGS. 6-9 wherein third dilator 200 can freely glide over second dilator 150. Although gaps between inner and outer dilator surfaces are sufficient to pass one dilator over the other, these gaps are minimized to prevent soft tissue from embedding within the gaps as increasingly larger dilators are advanced down the surgical axis.

The length of second dilator 150 is preferably sized wherein when stop surface 111 abuts against bone, grip portion 109 is fully exposed above the patient's skin as well as above the entire proximal end of third dilator 200. The length of first dilator 101 exceeds both the second dilator 150 and third dilator 200 wherein when first dilator 101 stop surface 111 abuts against bone, first dilator 101 grip portion 109 is fully exposed above proximal end 108 of second dilator 150.

FIGS. 6, 7, 8 & 9 illustrate views of a preferred embodiment of the third dilator 200 (e.g. the final dilator according to the example embodiments described herein). The third dilator 200 comprises an elongated body 106 with an inner elongated wall 110 defining a central aperture 220. This central aperture 220 is of sufficient diameter to slide over surface 107 of second dilator 150 as described previously and in addition is sufficient to provide passage for pedicle screw 151 and screw insertion instruments 153 such as those seen in FIGS. 20 & 21. An outer surface 107 resides on the elongated body 106 of the third dilator 200. The body 106 terminates at proximal screw face 224 on the proximal end 108.

The third dilator 200 comprises one or more fixator portions 201. In this embodiment, the fixator 201 is an extension of the proximal dilator body 106 in the form of a fixation boss 202. The boss 202 comprises a top surface 204, a bottom surface 205, and a side wall 208. An inner wall 203 defines an aperture 207 extending through the top 204 and bottom surfaces 205.

Figure 8:
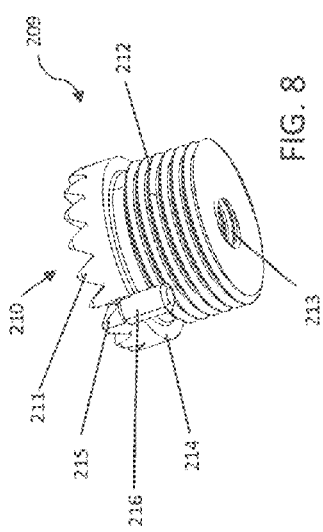
FIG. 8 is a front perspective close up view of an example embodiment of a fixator used in a third dilator.

The aperture 207 may comprise threads 206 and is configured to house a fixator lock 209 portion (FIG. 8). The fixator lock 209 comprises an elongate body 212 to be received in aperture 207. The outer surface of elongate body 212 has threads complementing those threads 206 in aperture 207 for a threaded engagement. Alternatively, fixator lock 209 may utilize a press fit when non-threaded.

An inner wall 213 defines a central threaded aperture through body 212. A fixator face 210 is illustrated here in the form of radially spaced inclined teeth 211. A stop 214, in the form of a ridge abuts the fixator lock top surface 204 when fully seated into aperture 207. A notch 215 partially houses interference locking pin 216 along with bore 218 in top surface 204 by press fit. The pin 216, when pressed into position prevents derotation and thus loosening of fixator lock 209 once seated in fixation boss 202.

Through the fixator face 210 is stabilization bore 219. This bore 219 extends down from fixator face 210. When used during surgery, the fixator lock 209 is the site for attachment of a fixation apparatus such as an A-arm which on one end is clamped to the surgical table or other immovable apparatus. The free end of the A-arm comprises a locking fixator with locking features complementing the fixator lock 209 described herein. For example, the free end of an A-arm may comprise a threaded fastener for advancing in the threaded inner wall 213, along with a post for housing within stabilization bore 219, and fixator face complementary to fixator face 210. Tightening of said fastener draws the A-arm tight to the fixator lock therein securely fixing the fixator lock 209 to the A-arm. According to the example shown, a plurality of fixators 201 with various size fixator locks 209 are included.

In this embodiment wherein the fixator lock 209 is formed as a separate part of third dilator 200, the opportunity exists to choose a material of manufacture having a strength and hardness that is highly resistant to wear. For example, the body 106 of dilator 200 may be manufactured from an anodized aluminum or a polymer like Radel, whereas the fixator lock 209 of FIG. 8 may be a stainless steel. The fixator portion 201 of third dilator 200 may take many other forms suitable for fixing the dilator 200 in a predetermined position during surgery. For example, in an alternate embodiment (not shown), the fixator face 210 may be machined into top surface 204 along with stabilization bore 219 and threaded inner wall 213 wherein the A-arm clamps directly to the fixator face 210 integral with fixation boss 202.

As an alternate form of fixator 201 (not shown), one or more elongated channels integral to outer dilator surface 107 and parallel with axis E may be utilized to house fixation pins that thread or penetrate directly into the bone therein holding third dilator tight to the bone surface. In yet another alternative, the fixator 201 may be in the form of a post extending outward radially about axis E from surface 107 at the proximal end 108 of third dilator 200. In yet another alternative, with an absence of fixation bosses 202, the fixator 201 may be in the form of dilator surface 107 at the proximal end 108 of third dilator 200. In this alternative configuration, the free-end of the A-arm may comprise a circumferential clamp configured to encircle the outer circumference of the tube. In another alternate embodiment, instead of (or in addition to) a fixator, the third dilator may be provided with a handle that me be used by the surgeon or assistant to hold the third dilator in the desired position.

Figure 7:
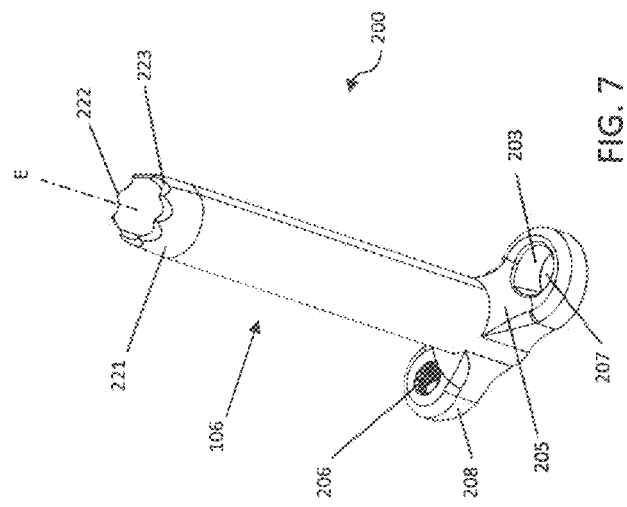
FIG. 7 is a bottom perspective view of a the third dilator of FIG. 6.
Figure 6:
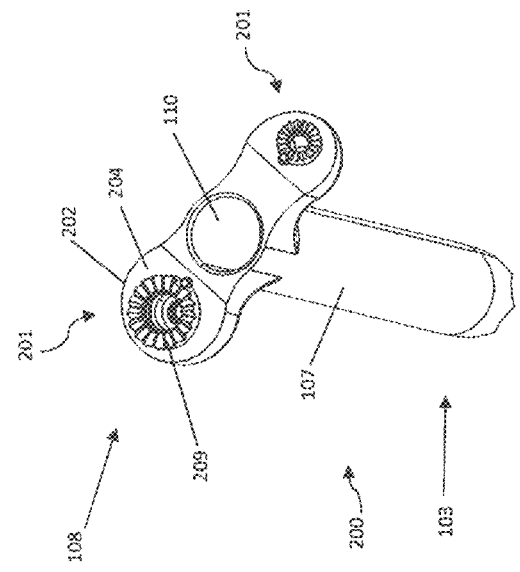
FIG. 6 is a top perspective view of an example embodiment of a third dilator.
Figure 20:
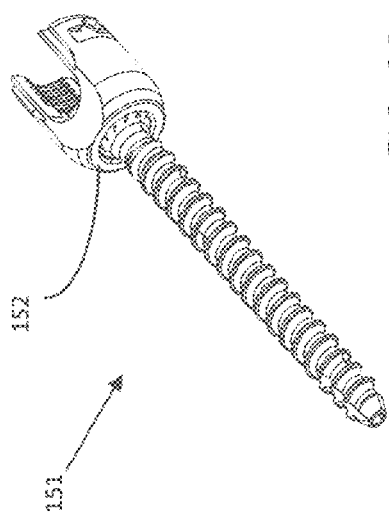
FIG. 20 is a front perspective view of a pedicle screw.
Figure 21:
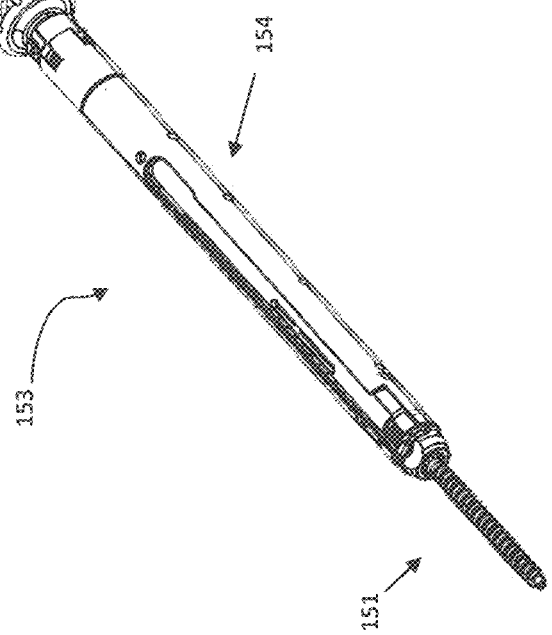
FIG. 21 is a front perspective view of a pedicle screw with associated insertion instruments used in minimally invasive procedures.

As illustrated in FIG. 7, the third dilator 200 has an outside taper 221 to improve movement through tissue that thins into scalloped teeth 222 at distal end 103. The teeth 222 may be sharpened 223. These teeth 222 lodge into bone when third dilator 200 is fully advanced into the surgical site and serve as yet another means to fix the dilator 200. It is not necessary that teeth 222 all reside in the same plane since the pedicle bone surface may not necessarily be flat. Therefore the teeth 222 may be profiled to best fit the contour of the pedicle bone surface. Although the example embodiment of the third dilator includes a flat (unsloped) distal tip with teeth serrations, an alternative option may include sloped end (with or without teeth serrations) that would approximate the slope of the sacrum adjacent the S1 pedicle.

The dilators may be manufactured of materials such as polymers (e.g. Radel), carbon fiber, aluminum, titanium, or stainless steel alloys. The instruments used herein are preferably manufactured from aluminum, titanium or stainless steel alloys. Other materials having suitable performance characteristics may also be used.

Illustrated in FIGS. 10 and 11 is a preferred embodiment of a blunt tip probe 300 configured to slide within inner cannula wall 110 of second dilator 150. The probe 300 comprises an elongated body 301 with central cannula 302 along axis B extending the entire length of body 301. The cannula 302 defines an inner wall 303 of said elongated body 301. At the distal end 103 of probe 300, is a blunt tip 304 illustrated in FIG. 11 having a bulbous end 305. Blunt tip 304 may include one or more external serrations 306 to assist with pilot hole extension when the instrument is advanced through cancellous bone. At distal end of blunt tip 304 is distal surface 308 utilized to push through cancellous bone during pilot hole extension.

Probe 300 is configured to slide within inner elongated walls 110 of second dilator 150. The probe arm 309 portion is a distal end portion 103 of body 301 that narrows for a length of D which is sufficient to span from the outer surface of the pedicle to the anterior side of the anterior cortical wall for pilot hole extension through the cancellous bone. Proximal to the probe arm 309 may be a diameter transition 310 wherein the diameter of outer surface 311 of body 301 increases to a diameter just less than inner cannula diameter of the inner elongated wall 110 of second dilator 150. This diameter transition 310 may be in different forms such as a fillet as illustrated in FIG. 10, a chamfer, or a step. The combination of the narrow probe arm 309 with blunt tip 305 and the thicker body 301 permits the probe to advance through cancellous bone to extend the pilot started by the Jamsheedi with enough rigidity to withstand bending (as opposed to typical ball tip probes), such that length measurements taken from the probe are not skewed, while lacking the ability under normal insertion forces to penetrate through cortical bone.

On outer surface 311 is probe reference 312, illustrated in FIG. 10 as a series of black circumferential etched lines but may take other forms. For example, probe reference 312 may be in the form of grooves, hash marks, or depressions, and may be color coded or marked with alpha-numeric characters. The reference marks 312 are tied to the length of the second dilator and are indicative of the length to which the distal end of the probe advances beyond the distal end of the second dilator 150. Since the distal end of the second dilator rests against the pedicle surrounding the pilot hole, the distance the distal end of the probe 300 extends beyond the distal end of the second dilator 150 (when the probe is fully advanced through the vertebra to the anterior cortical wall) corresponds to the depth of the vertebra from the outer wall of the pedicle to the inner surface of the anterior cortical wall.

Probe 300 may also comprise a neuromonitoring connection 313 configured for attachment of neuromonitoring accessory (e.g. stimulation clip, not shown) for monitoring pedicle integrity (e.g. detecting breaches of the pedicle wall) during advancement of the probe through the pedicle. In this embodiment illustrated in FIG. 10, connector 313 is in the form of a conductive circumferential body 301 for attachment of a stimulation clip. Connector 313 is typically located near proximal end 108 to avoid interfering with the surgical entry site.

At the proximal end 108 of probe 300 is a grip portion 317 configured for gripping by the surgeon. In this embodiment, grip portion 317 is in the form of features for attachment of a removable handle (not shown). Body 301 comprises one or more torque faces 315 for transmitting torque from the handle through body 301, one or more lock faces 314 for temporary locking of the handle to body 301, and an axial face 318 to transmit axial forces from the handle down body 301. Alternatively, body 301 may extend proximally and be formed into the shape of a handle or be configured to accept a handle thereon such as in the form of a rubber grip.

Illustrated in FIGS. 12-14 is a preferred embodiment of a bone tap 400 configured to slide within inner cannula wall 110 of second dilator 150. Bone tap 400 comprises an elongated body 401 with central cannula 402 along axis F extending the entire length of body 401. The cannula 402 defines an inner wall 403 of said elongated body 401. At the distal end 103 of bone tap 400, is tap shaft 404 shown in FIG. 12 and that further comprises fluted 409 tap tip 439 with radial cutting teeth 407 formed by tap thread 408 and cutting face 405 that includes one or more forward cutting teeth 406 to assist with penetration of the anterior cortical wall.

Bone tap 400 is configured to slide within inner elongated walls 110 of second dilator 150. The tap arm 410 portion is a distal end portion 103 of body 401 that narrows for a length D as introduced earlier. Length D is sufficient in length to span from the outer surface of the pedicle to the anterior side of the anterior cortical wall for taping threads along pilot hole. Proximal to the tap arm 410 may be a diameter transition 419 wherein the diameter of outer surface 411 of body 401 increases to a diameter just less than inner cannula diameter created by the inner elongated wall 110 of second dilator 150. For example, this diameter transition 419 may be in the form of a fillet as illustrated in FIG. 12, a chamfer, or a step.

On outer surface 411 is tap reference 412 illustrated in FIG. 13 as a series of hash lines but may take other forms. For example, tap reference 412 may be in the form of grooves, circumferential etched lines, or depressions, and may be color coded or marked with alpha-numeric characters suitable for determining the depth of the instrument with respect to anatomical structures of the patient or to other instruments.

Tap 400 also includes a safety stop 421 also illustrated in FIGS. 13, 15 and 16. Safety stop 421 adjusts along depth ladder 422 corresponding to the tap reference 412. In this embodiment, depth ladder 422 comprises a generally rectangular cross-section with a plurality of depth notches 423 on lateral sides of the rectangle configured to serve as incremental stop positions engaging safety stop 421. As seen in FIG. 15, safety stop 421 comprises a housing 426 with radial surface 427 and a pair of opposing side surfaces 424. Centered along axis K, ladder bore 425 with profile complementing depth ladder 422 extends through opposing side surfaces 424. Generally perpendicular to ladder bore 425, release bore 428 extends through radial surface 427 to house release 429. Release 429 in this embodiment has a generally a square shaped ring body 430 with an exposed activation surface 431, a pair of opposing legs 432, and a bottom strut 433. On the backside of bottom strut 433 is spring surface 434. Within ring body 430, resides ring bore 435 of a generally rectangular shape. Extending from inside the legs 432 and bottom strut 433 are cogs 436. Each cog 436 has opposing side surface 437 and top surface 438.

In use, release 429 is housed in release bore 428. A biasing element (not shown), preferably in the form of a spring and situated within release bore 428 and behind spring surface 434, biases release 429 outward causing cogs 436 to move towards central axis K for engagement of depth notches 423 therein causing safety stop 421 to lock in desired position along depth ladder 422. Side surface 424 serves as a stop against proximal stop surface 112 of second dilator 150 wherein tap is limited to a depth predetermined by the user. Accordingly, the depth stop can be set based on the measured depth of the vertebra such that the distal end may be advanced into but not through the anterior cortical wall.

While shown according to one example embodiment, the safety stop 421 may take on a variety of forms. For example, it may be in the form of a resilient ring that expands upon force of the user, adjusted to a new position, then contracts back around a complementary depth ladder recess. As another alternative, stop 421 may be in the form of a threaded nut translating up and down a threaded depth ladder. Yet another alternative for the button is in the shape of a ball detent mechanism, in which this mechanism contains ball bearings that lock into mating grooves on the instrument shaft. Ball detent mechanisms are a popular choice in similar designs.

Tap 400 may also comprise a neuromonitoring connection 413 configured for attachment of a neuromonitoring accessory (e.g. stimulation clip, not shown) for monitoring pedicle integrity (e.g. detecting breaches of the pedicle wall) during advancement of the tap through the pedicle. In this embodiment illustrated in FIG. 12, connector 413 is in the form of a conductive circumferential body for attachment of a stimulation clip. Connector 413 is typically located near proximal end 108 to avoid interfering with the surgical entry site.

At the proximal end 108 of tap 400 is a grip portion 417 configured for gripping by the surgeon. In this embodiment, grip portion is in the form of features for attachment of a removable handle (not shown). Body 401 comprises one or more torque faces 415 for transmitting torque from the handle through body 401, one or more lock faces 414 for temporary locking of the handle to body 401, and at least one axial face 418 to transmit axial forces from the handle down body 401. Alternatively, body 401 may extend proximally and be formed into the shape of a handle or be configured to accept a handle thereon such as in the form of a rubber grip.

A preferred embodiment of a bone reamer 500 is illustrated in FIG. 17. Reamer 500 comprises an elongate body 501 with outer surface 511. A central cannula 502, sufficient to house a guide wire, defines an inner wall of the cannula. At distal end 103 is reamer head 504 configured at the preferred trajectory for removing uneven or angled bone at the surface of the pedicle when driven under rotation against a bone surface. Reamer head 504 comprises a distal face 505 to abut against the bone surface, one or more axial reamer blades 506 for shaving the surface of the bone, a radial bone channel 507 to house bone chips as they are cut, and axial channel 508 as a path for bone chips to move into chip pocket 509. At proximal end 108 the instrument is a handle portion 510 configured for grasping by the user. The handle may include a grip 512 here shown in the form of axial grooves or knurling in body 501.

FIGS. 18-19 illustrate a preferred embodiment of a contour probe 600. Contour probe 600 may be utilized to map irregularities of the pedicle surface if desired. This information may be used to determine whether reaming is desirable, the depth of reaming required, and bone to yoke 152 spacing that may be necessary for proper polyaxial motion of the pedicle screw yoke. Contour probe 600 comprises an elongate body 601 with an outer surface 602 of body 601. Central to body 601, an elongated cannula 605, sufficient to receive a K-wire, defines an inner wall 606 of the cannula. At the proximal end 604, a handle portion 607 may include a grip 608 here shown in the form of radial grooves or knurling in body 601 to improve grip of the instrument. At the distal end 603, is contour tip 609 laterally offset from axis P. The tip 609 comprises an elongated tip arm 610 and is preferably rounded at contact surface 611. A medial surface 612 resides on the inside of tip arm 610. The elongate body 602 is configured with a diameter to pass through the inner elongated walls 110 of second dilator 150 or may alternatively be configured with larger outer surface 602 diameter when used within third dilator 200. On outer surface 602 is contour reference 613 illustrated in FIG. 18 as a series of spaced grooves but may take other forms as described previously. With the contour probe advanced to the pedicle through the second dilator, the height of the proximal end of the probe relative to the second dilator adjusts as the tip 609 is rotated around the pedicle. If the height variation is substantial the surgeon may optionally choose to use reamer 500 prior to inserting the blunt probe 300, or prior to assessing the depth of the vertebra from the blunt tip probe prior to tapping.

The following exemplary steps of a procedure using the instruments described above provides an example method for safely and reproducibly achieving bi-cortical screw fixation at the S1 vertebral body. While described with relation to the fixation at the S1 body, the same method may be used other vertebral levels as well. In the preferred embodiment, the method is two-fold beginning with determining the distance from the top most surface of the pedicle to the inner surface of the anterior cortical wall and in using this information to safely pierce the anterior cortex (anterior cortical wall) without extending the tap or screw anteriorly beyond the cortex further than necessary. Second, methods are described for maintaining guide at a stable and consistent trajectory such that tapping and screw insertion may be performed without advancement over a K-wire (which can be inadvertently advanced through the anterior cortical during such steps).

In the preferred embodiment, the method begins with placement of a guidewire (K-wire) in a predetermined location in the sacral (S1) pedicle 700 (FIG. 22). The K-wire 100 acts to guide instruments and establish the screw trajectory to this location. The skin may be incised over the pedicle at the desired entry point (e.g. approximately 1 cm lateral to the pedicle). A Jamsheedi needle (not shown) is inserted into the vertebra at the predetermined location. The stylet of the Jamsheedi is removed followed by insertion of the K-wire 100 though the remaining Jamsheedi cannula. The K-wire 100 is inserted a distance one half the depth of the vertebrae or a distance to assure it is firmly seated within the bone without the K-wire 100 tip piercing beyond the distal cortical bone wall. To prevent injury to tissues adjacent the distal cortical wall of the bone when inserting the Jamsheedi and/or guidewire, their position may be monitored by intra-operative fluoroscopy and neurophysiology monitoring equipment.

At least one, and preferably a series of sequential dilators are used to dilate down to the pedicle over the K-wire 100. In the preferred embodiment, the surgeon grasps the first dilator 101 and directs aperture 105 over the loose end of K-wire 100. The surgeon then advances the first dilator 101 down the surgical path stretching through the soft tissues surrounding the K-wire 100 until first dilator stop surface 111 abuts the bone. Inner elongated wall 110 of second dilator 150 is then directed over outer surface 107 of first dilator 101, again stretching through the surrounding soft tissue until stop surface 111 of second dilator 150 abuts the targeted S1 pedicle. The central aperture 220 of third dilator 200 is then advanced down over second dilator surface 107 therein fully stretching surrounding soft tissue out of its path until teeth 222 contact the S1 pedicle bone surface.

As an option (not shown), the surgeon may utilize contour probe 600 to map the pedicle surface for irregularities. This is performed by removing the second dilator 150 and first dilator 101 away from the surgical site. Elongated cannula 605 of contour probe 600 is then advanced over K-wire 100 until contact surface 611 abuts the bone. At the anticipated screw trajectory, the user then monitors depth changes in reference 613 compared to proximal screw face 224 of third dilator 200 as contour probe 600 is rotated over the surface of the pedicle. Small to no reference change indicates little surface height variation whereas large reference changes indicate large changes in surface height. In the case of large changes in pedicle surface height, the surgeon may choose to level the pedicle surface using a bone reamer 500 to create a flat bone surface before reinsertion of second dilator 150 in later steps (FIG. 24). Utilizing the bone reamer creates a flat bone surface against which the second dilator sits to facilitate depth measurement with the blunt tip probe 300. The user advances central cannula 502 of bone reamer 500 over K-wire 100 until distal face 505 abuts the bone surface and places rotational and axial force through handle 510 toward the vertebrae causing reamer blades 506 to cut the bone and resulting in a level surface. The bone reamer 500 is then removed. Bone chips may be removed from the site by hand instruments or suction. Second dilator 150 is then reinserted down central aperture 220 of third dilator 200 until contacting pedicle bone surface.

In subsequent steps, the pilot hole initially created by the Jamsheedi needle through the posterior cortical wall of the pedicle is extended through the cancellous bone to the inner surface of the anterior cortical wall (FIG. 25). In this step, neuromonitoring may be performed to ensure the pilot hole extends distally through the pedicle and does not breach the pedicle wall. Central cannula 302 of blunt-tip probe 300 is advanced over K-wire 100 into the pilot hole created by the jamsheedi. The surgeon, using grip portion 317, continues with controlled advancement of probe 300 through the softer cancellous bone until a harder stop is felt through the instrument indicating abutment of distal surface 308 with the inner surface of the anterior cortical wall. A depth reading is noted from probe reference 312 in view of proximal stop surface 112 of second dilator 150. In this embodiment, the references on the probe are calibrated wherein the user can directly read a depth 'Y' from the reference where the reference aligns with the proximal stop surface 112 indicating the depth of the distal surface 308 of probe 300 beyond the distal stop surface 111 of the second dilator 150, which corresponds to the depth of the vertebra from posterior pedicle wall to inner surface of the anterior cortical wall.

With the blunt-tip probe 300 now defining the correct pilot hole trajectory, third dilator 200 is concentrically aligned to this path, by virtue of the second dilator 150 being aligned with the probe, and fixed in place by attachment of fixator lock 209 of third dilator 200 to an articulating arm (A-arm) or compatible handle. In this embodiment, the articulating arm (not shown) locks against fixator face 210 with screw fixation through stabilization bore 219 and threading into inner wall 213 (FIGS. 6-9). For additional stability, the surgeon may choose to drive or tap proximal screw face 224 of third dilator 200 to seat teeth 222 in pedicle bone as illustrated in FIG. 23. By locking the third dilator 200 with an A-arm, the hole trajectory is defined therein providing for concentric alignment of the pilot hole, tap, and screw placement. K-wire 100 and blunt tip probe 300 are no longer necessary and are removed.

Figure 28:
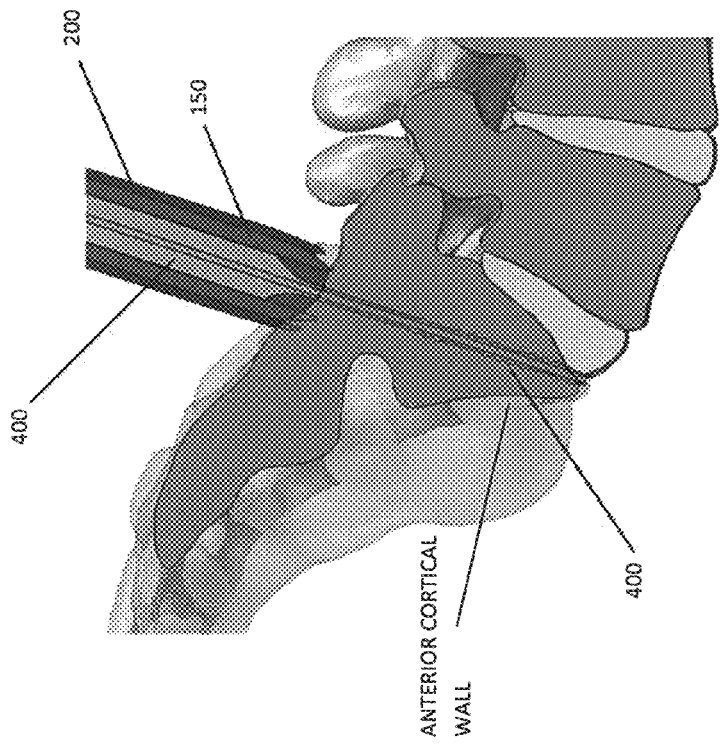
FIG. 28 is a cross-sectional sagittal plane view through the pedicles of FIG. 27 illustrating the tap creating thread in the pilot hole in the vertebrae.
Figure 27:
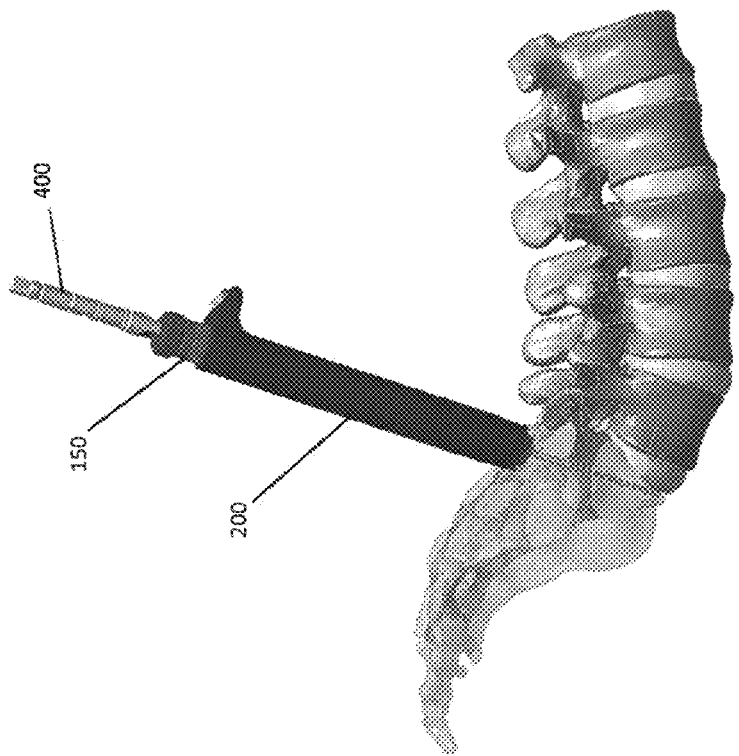
FIG. 27 is a lateral view of a tap creating thread in the pilot hole in the vertebrae, according to the example method referenced in FIG. 23.

The pilot hole is now tapped and anterior cortical wall pierced (FIG. 28). Bone tap 400 is utilized to tap the pilot hole in the bone in preparation of screw 151 insertion. Tap 400 is also used to provide a controlled method of piercing the anterior cortical wall. As discussed earlier, tap reference 412 and probe reference 312 may be calibrated to provide the same depth reading on each instrument when at identical bone depths while also indicating the depth of penetration into the bone. Bone tap 400 features optional safety stop 421. In this embodiment, the safety stop is adjustable in 2.5 mm increments.

In the next step of the method, depth 'Y' is recalled. Assuming for example, the anterior cortical wall to be 2.5 mm thick, 2.5 mm is added to depth reading 'Y' for sum 'Q'. Sum Q represents the tap depth required to pierce the anterior cortical wall. Distal facing side surface 424 of safety stop 421 is aligned with the tap reference 412 value equal to sum Q by depressing activation surface 431 and sliding safety stop 421 along depth ladder 422. For example: If the second blunt-tip probe reference 312 reading is 45 mm, then distal facing side surface 424 is aligned with reading 47.5 mm. This step provides controlled piercing of the anterior cortical wall without the tap over extending anteriorly.

Neuromonitoring may again be performed during tapping to ensure the tap does not breach the pedicle wall. Tap shaft 404 of bone tap 400 is led to pilot hole through the second dilator, along the trajectory fixed via the third dilator, and advanced with rotation causing tap thread 408 to tap pilot hole. When distal facing side surface 424 abuts proximal stop surface 112 of second dilator 150, the pilot hole is threaded to the desired depth. Rotation of tap can now be reversed and tap 400 removed from surgical path, followed by the second dilator.

Based on depth measures obtained earlier such as value Q or Y, the surgeon will then choose an appropriate screw length for bi-cortical purchase. The surgeon may choose a screw 151 length to compensate for any amount of spacing she may desire between yoke 152 and the pedicle bone surface for full poly-axial motion of the yoke 152. The surgeon may also choose a slightly longer screw to assure threads have full purchase in the anterior cortical wall yet have minimal protrusion.

Pedicle screw 151 with attached insertion instruments 153 is now centered then advanced down screw path trajectory defined by central aperture 220 of fixed third dilator 200 and pre-threaded pilot hole. Because the screw length is selected based on the predetermined vertebra depth, monitoring insertion depth of the inserter is not necessary. However, the screw insertion instruments may also have an inserter reference 154 similar to that seen on other instruments. Because the second dilator 150 is removed and cannot be utilized as a depth reference, however, the reference on the screw inserter may be made to account for the difference in length between the second dilator and the third dilator. The above described steps may be completed for positioning of each pedicle screw to be implanted and the fixation construct may be completed with rod placement and construct locking.

While the present invention has been shown and described in terms of preferred embodiments thereof, it should be understood that this invention is not limited to any particular embodiment and that changes and modifications may be made without departing from the true spirit and scope of the invention as defined in the appended claims.

What is claimed is:

1. A method for bi-cortical screw fixation in a vertebrae comprising the steps of:
   inserting a guidewire into a pre-determined location in a pedicle defining an initial surgical path;
   advancing one or more inner dilators over said guidewire down to the bone surface of the pedicle to expand soft tissues surrounding said guidewire;
   advancing over the one or more inner dilators a final dilator having an lumen sized to pass a minimally invasive pedicle screw;
   removing at least one of the one or more inner dilators;
   advancing a probe through the final dilator and any remaining inner dilators, the probe having a blunt tip and a visual reference scale for reading against a visual reference located on at least one of the final dilator and a remaining inner dilator, the blunt tip of the probe being advanced through the pedicle and cancellous bone of the vertebral body to create a guide hole until said blunt leading end of the probe contacts the anterior cortical wall of the vertebrae;
   establishing a fixed trajectory aligned with the guide hole formed by the advancement of the blunt tip of the probe through the vertebral body by fixing the position of said final dilator while said probe is still in positioned within said guide hole; determining a depth of the vertebra by comparing the visual reference scale on the probe against the visual reference located on the final dilator or remaining inner dilator;
   removing the guidewire and blunt tip probe from surgical site and inserting a bone tap through the final dilator along the fixed trajectory and tapping the guide hole while monitoring for breach of the pedicle wall with a neuromonitoring system coupled to the tap, the bone tap having a depth stop set to a predetermined depth based on the determined depth of the vertebra
   removing bone tap and all dilators except final dilator from surgical path;
   advancing pedicle screw of a length selected based upon the determined depth of the vertebra down the tapped guide hole such that a distal end of the screw is seated in the anterior cortical bone of vertebrae.

2. The method of claim 1, wherein the
   a spring biased release button of the adjustable depth stop engages notches along the body of the bone tap to position the adjustable depth stop in a selected position along the length of the body of the bone tap, the selected position corresponding to a position in which a lower surface of the adjustable depth stop will abut a proximal surface on at least one of the final dilator and a remaining dilator when a distal end of the tap is positioned within the anterior cortical wall.

3. The method of claim 1, further comprising the step of:
   utilizing a reference on a body of a screw insertion instrument to advance the pedicle screw to a predetermined depth corresponding to the determined vertebra depth.

4. The method of claim 1, wherein fixing the position of said final dilator includes a free end of an adjustable fixation arm attached to the final dilator, the end of the fixation arm opposite the free end being fixed to a stationary object.

5. A method for bi-cortical screw fixation in a vertebrae comprising the steps of:
   inserting a guidewire into a pre-determined location in a pedicle defining an initial surgical path;
   advancing one or more inner dilators over said guidewire down to the bone surface of the pedicle to expand soft tissues surrounding said guidewire;
   advancing over the one or more inner dilators a final dilator having an lumen sized to pass a minimally invasive pedicle screw;
   removing at least one of the one or more inner dilators;
   advancing a probe through the final dilator and any remaining inner dilators, the probe having a blunt tip and a visual reference scale for reading against a visual reference located on at least one of the final dilator and a remaining inner dilator, the blunt tip of the probe being advanced through the pedicle and cancellous bone of the vertebral body to create a guide hole until said blunt leading end of the probe contacts the anterior cortical wall of the vertebrae;
   determining a depth of the vertebra by comparing the visual reference scale on the probe against the visual reference located on the final dilator or remaining inner dilator;
   removing the blunt tip probe from the surgical site and advancing a bone tap to tap the guide hole, the bone tap having a depth stop set to a predetermined depth based on the determined depth of the vertebra;
   removing bone tap and all dilators except final dilator from surgical path;
   advancing pedicle screw of a length selected based upon the determined depth of the vertebra down the tapped guide hole such that a distal end of the screw is seated in the anterior cortical bone of vertebrae.

6. The method of claim 5, wherein the
   a spring biased release button of the adjustable depth stop engages notches along the on body of the bone tap to position the adjustable depth stop in a selected position along the length of the body of the bone tap, the selected position corresponding to a position in which a lower surface of the adjustable depth stop will abut a proximal surface on at least one of the final dilator and a remaining dilator when a distal end of the tap is positioned within the anterior cortical wall.

7. The method of claim 5, further comprising the step of:
   utilizing a reference on a body of a screw insertion instrument to advance the pedicle screw to a predetermined depth corresponding to the determined vertebra depth.

8. The method of claim 5, further comprising the step of:
   removing said guidewire before advancing the pedicle screw down said pilot hole.

9. The method of claim 5, wherein fixing the position of said final dilator includes attaching a free end of
   an adjustable fixation arm to the final dilator, the end of the fixation arm opposite the free end being fixed to a stationary object.

10. The method of claim 5, further comprising the step of:
    monitoring the advancement of the tap with a neuromonitoring coupled to said bone tap to detect breaches in the pedicle wall.

* * * * *